(12) United States Patent
Lin et al.

(10) Patent No.: US 12,262,947 B1
(45) Date of Patent: Apr. 1, 2025

(54) SYSTEMS AND METHODS FOR RETINAL IMAGING

(71) Applicants: Wei-Chiang Lin, Miami, FL (US); Shuliang Jiao, Miami, FL (US); Rui Zhou, Miami, FL (US); Nikolaos Tsoukias, Miami, FL (US)

(72) Inventors: Wei-Chiang Lin, Miami, FL (US); Shuliang Jiao, Miami, FL (US); Rui Zhou, Miami, FL (US); Nikolaos Tsoukias, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/901,661

(22) Filed: Sep. 30, 2024

(51) Int. Cl.
*A61B 3/12* (2006.01)
*A61B 3/00* (2006.01)
*A61B 3/10* (2006.01)

(52) U.S. Cl.
CPC ............ *A61B 3/1225* (2013.01); *A61B 3/005* (2013.01); *A61B 3/102* (2013.01)

(58) Field of Classification Search
CPC ........ A61B 3/1225; A61B 3/005; A61B 3/102

USPC ......................................................... 351/206
See application file for complete search history.

(56) References Cited

U.S. PATENT DOCUMENTS

| | | | | |
|---|---|---|---|---|
| 2004/0207811 | A1* | 10/2004 | Elsner | A61B 3/1025 351/205 |
| 2009/0244482 | A1* | 10/2009 | Elsner | A61B 3/1025 351/206 |
| 2013/0308098 | A1* | 11/2013 | Levecq | A61B 3/1015 351/206 |
| 2014/0146288 | A1* | 5/2014 | Anand | A61B 3/0008 351/207 |
| 2014/0192324 | A1* | 7/2014 | Straub | G01N 21/4795 351/206 |
| 2017/0323481 | A1* | 11/2017 | Tran | H04N 23/611 |
| 2019/0290125 | A1* | 9/2019 | Amelink | A61B 3/12 |

\* cited by examiner

*Primary Examiner* — Mohammed A Hasan
(74) *Attorney, Agent, or Firm* — SALIWANCHIK, LLOYD & EISENSCHENK

(57) ABSTRACT

Systems and methods for retinal imaging are provided. A heads-up display (HUD) can be integrated with advanced retinal imaging modalities, including optical coherence tomography (OCT) and fundoscopy (e.g., fluorescence fundoscopy). The HUD can serve as a crucial component of this approach, offering several key functionalities (e.g., a fixation target and/or a means for dark adaptation).

8 Claims, 4 Drawing Sheets

Two-eye implementation

Single-eye implementation

SYSTEMS AND METHODS FOR RETINAL IMAGING

BACKGROUND

Retinal imaging creates high-quality digital images of the inner, back surface of an eye and can be used for diagnostic purposes. Retinal imaging can be used to diagnose, for example, diabetes-related retinopathy, glaucoma, and macular degeneration.

BRIEF SUMMARY

Embodiments of the subject invention provide novel and advantageous systems and methods for retinal imaging. A heads-up display (HUD) can be integrated with advanced retinal imaging modalities, including Optical Coherence Tomography (OCT) and fluorescence fundoscopy. The HUD can serve as a crucial component of this approach, offering several key functionalities.

In an embodiment, a system for retinal imaging can comprise: a retinal imaging device; and a HUD disposed proximate to the retinal imaging device, the HUD being configured to provide a fixation target for a patient during retinal imaging. The HUD can also be configured to provide stimulation (e.g., light at one or more wavelengths with one or more levels of intensity) during retinal imaging (e.g., while imaging the function of the retina). The system can further comprise a dichroic mirror configured to reflect light (e.g., near infrared (NIR), infrared (IR), and/or visible light) from an eye of the patient to the retinal imaging device during retinal imaging. The dichroic mirror can also be configured to direct the light (e.g., NIR light) from the retinal imaging device to the retina of the patient during retinal imaging. The retinal imaging device can be, for example, an OCT device (e.g., an NIR OCT device and/or a spectral domain (SD) OCT device, such as a fiberoptic SDOCT). The system can further comprise a galvanometer (e.g., an XY galvanometer) in operable communication with the OCT device. The system can further comprise a relay lens disposed between the OCT device and the HUD. The retinal imaging device can, for example, a fundoscopy device (e.g., a fluorescence fundoscopy device). The fundoscopy device can comprise an image sensor (e.g., an NIR, IR, and/or visible light image sensor), such as a camera. The system can further comprise a relay lens and/or a ring illumination element (e.g., an NIR illumination element configured to provide NIR light) disposed between the image sensor and the HUD. The HUD can be a two-eye HUD or a one-eye HUD.

In another embodiment, a method for retinal imaging on a patient can comprise: providing a retinal imaging device; disposing a HUD to provide a fixation target for the patient; and operating the retinal imaging device to receive light (e.g., NIR, IR, and/or visible light) reflected from an eye of the patient. The HUD can also provide stimulation (e.g., light at one or more wavelengths with one or more levels of intensity) during retinal imaging (e.g., while imaging the function of the retina). The retinal imaging device can have any of the features described in the previous paragraph, and the HUD can have any of the features described in the previous paragraph. The method can further comprise disposing a dichroic mirror between the eye of the patient and a display screen of the HUD, the dichroic mirror reflecting the light from the eye of the patient to the retinal imaging device. The dichroic mirror can also direct the light (e.g., NIR light) from the retinal imaging device to the retina of the eye of the patient during retinal imaging. The retinal imaging can be, for example, functional retinal imaging. The method can further comprise providing dark adaptation with the HUD prior to operating the retinal imaging device. The method can further comprise analyzing the retinal imaging results to: diagnose one or more retinal and neurological diseases, including but not limited to diabetic retinopathy, glaucoma, retinitis pigmentosa, hypertensive retinopathy, retinopathy of prematurity, Alzheimer's disease, multiple sclerosis, Parkinson's disease, and/or amyotrophic lateral sclerosis; perform one or more visual function tests, including but not limited to amblyopia, squint, vision field inspection, and/or distortion; perform a vision science analysis/study; and/or perform a psychophysical analysis/study.

DETAILED DESCRIPTION

Embodiments of the subject invention provide novel and advantageous systems and methods for retinal imaging. A heads-up display (HUD) can be integrated with advanced retinal imaging modalities, including Optical Coherence Tomography (OCT) and fundoscopy (e.g., fluorescence fundoscopy). The HUD can serve as a crucial component of this approach, offering several key functionalities.

The HUD can provide a precise fixation target, enhancing the accuracy and reproducibility of retinal imaging. This can enable researchers and clinicians to focus on specific areas of interest within the retina, facilitating detailed examination and analysis. Also, the HUD can be configured to deliver controlled light stimulation (to a wearer of the HUD) to select portions of the retina and/or the entire retina. The wavelength of the stimulation can be tunable, and the intensity of the stimulation can also be tunable. This optical stimulation induces specific responses in the retinal tissue, which can be captured and analyzed using the integrated advanced retinal imaging modalities.

The HUD can advantageously providing a straightforward means for dark adaptation, a critical requirement for retinal imaging with optical stimulation (i.e., functional retinal imaging). In order to perform functional retinal imaging, dark adaptation is needed to allow the retina's photoreceptors to become highly sensitive to low levels of light. Related art dark adaptation methods necessitate patients to remain in a dark room for a minimum of 30 minutes. In addition, related art approaches require the entire imaging process to be conducted in a dark environment, leading to practical inconveniences for both operators and patients. The HUD's ability to streamline dark adaptation directly not only enhances the overall convenience of the retinal imaging procedure but also simplifies logistics for operators.

By combining the HUD's fixation target with its capacity for precise optical stimulation and seamless integration with retinal imaging modalities, embodiments of the subject invention provide powerful tools for studying retinal function and structure. Embodiments also allow for dynamic assessment of the retina's response (both globally and locally) to light stimuli, opening new avenues for research and diagnosis in the fields of ophthalmology and biomedical engineering.

Figure 1A:
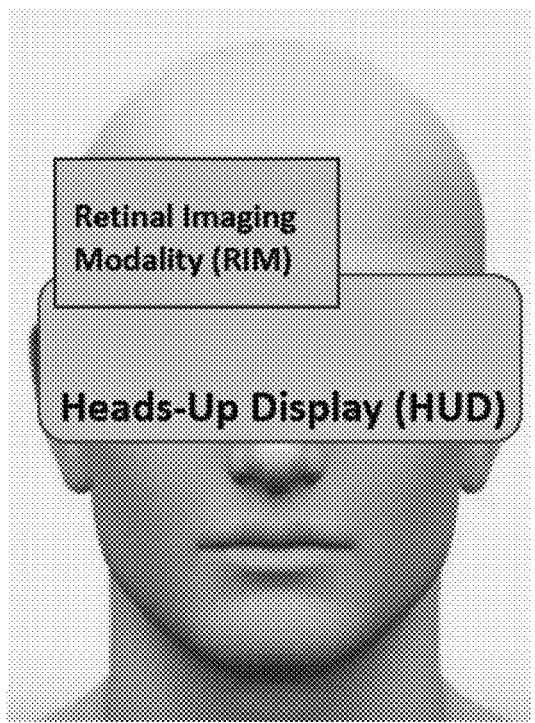
FIG. 1A shows a diagram of a two-eye implantation of a retinal imaging system, according to an embodiment of the subject invention.
Figure 1B:
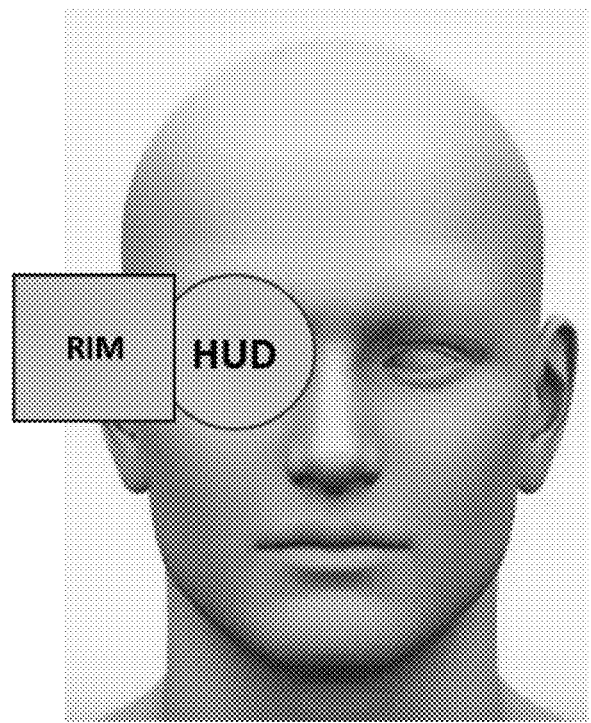
FIG. 1B shows a diagram of a one-eye implantation of a retinal imaging system, according to an embodiment of the subject invention.

The HUD can be a two-eye HUD or a one-eye HUD. FIG. 1A shows a diagram of a two-eye implantation of a retinal imaging system, according to an embodiment of the subject invention; and FIG. 1B shows a diagram of a one-eye implantation of a retinal imaging system, according to an embodiment of the subject invention. Referring to FIGS. 1A and 1B, a key advantage of the retinal imaging systems and methods of embodiments of the subject invention is the incorporation of a HUD. The HUD can be designed to enhance imaging capabilities and user experience by providing at least the following functionalities: a) offering a fixation target to stabilize the patient's (i.e., wearer's) gaze, thereby minimizing ocular movement and enabling operators to specify the retinal location for imaging; b) offering the option of localized or global stimulation conducive to functional retinal imaging; and c) supplying a user-friendly mechanism for facilitating dark adaptation.

Figure 2:
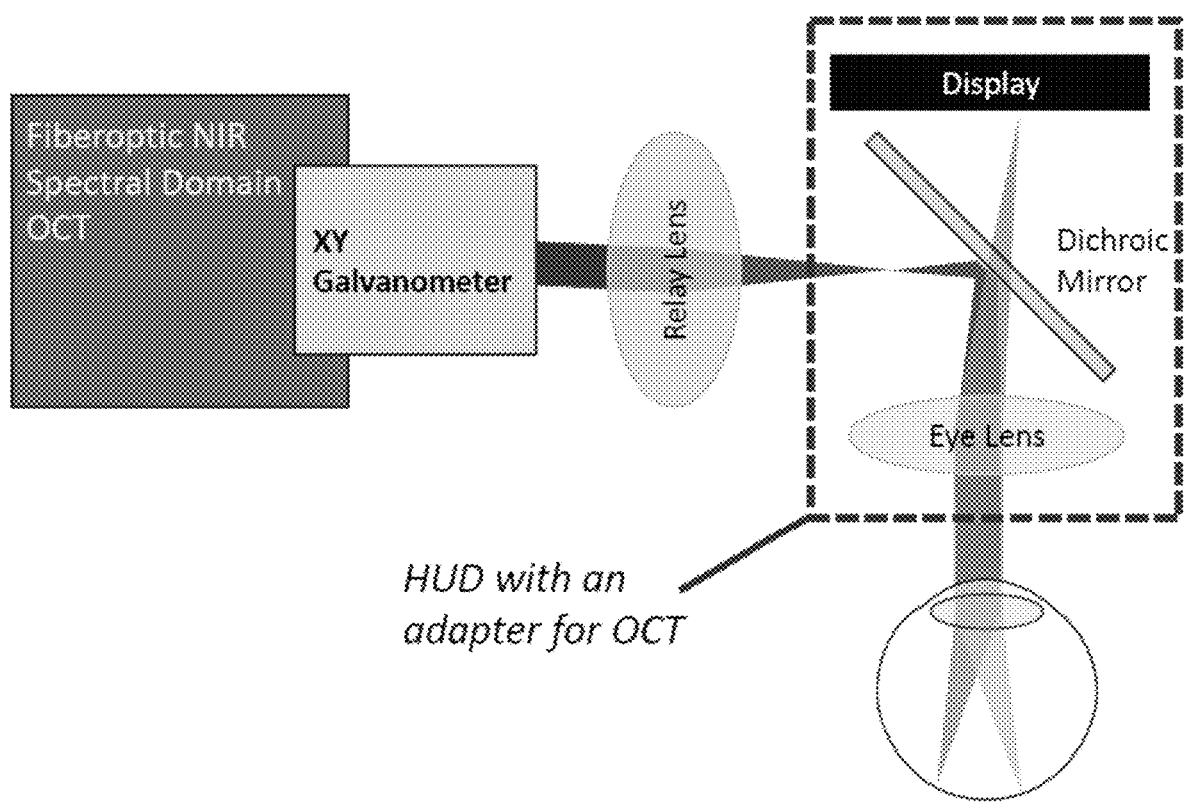
FIG. 2 shows a diagram of a retinal imaging system, according to an embodiment of the subject invention.

FIG. 2 shows a diagram of a retinal imaging system, according to an embodiment of the subject invention, in which OCT is integrated with a HUD. The OCT can be, for example, near infrared (NIR) OCT (e.g., fiberoptic NIR spectral domain OCT), though embodiments are not limited thereto. Referring to FIG. 2, the system can include an OCT device and a HUD. The system can further include a galvanometer (e.g., an XY galvanometer) and/or a relay lens disposed between the OCT device and the HUD. The HUD can include an adapter for OCT. The system can include a dichroic mirror, which may be part of the HUD. This system improves the accuracy of the retinal imaging process by allowing the operator (e.g., clinician, researcher, medical professional) to select the targeted retinal region, and by stabilizing the patient's gaze to reduce motion artifacts. Moreover, the HUD can provide the necessary optical stimulation for functional retinal imaging, making it a valuable tool for operators. The system can further include a processor and/or machine-readable medium in operable communication with the HUD and/or the OCT device; the processor and the machine-readable medium can be in operable communication with each other. The machine-readable medium can have instructions stored thereon that, when executed by the processor, perform analysis of the data received from the OCT device and/or the HUD. The system can also include a display (different from the HUD) for displaying results of the analysis.

Figure 3:
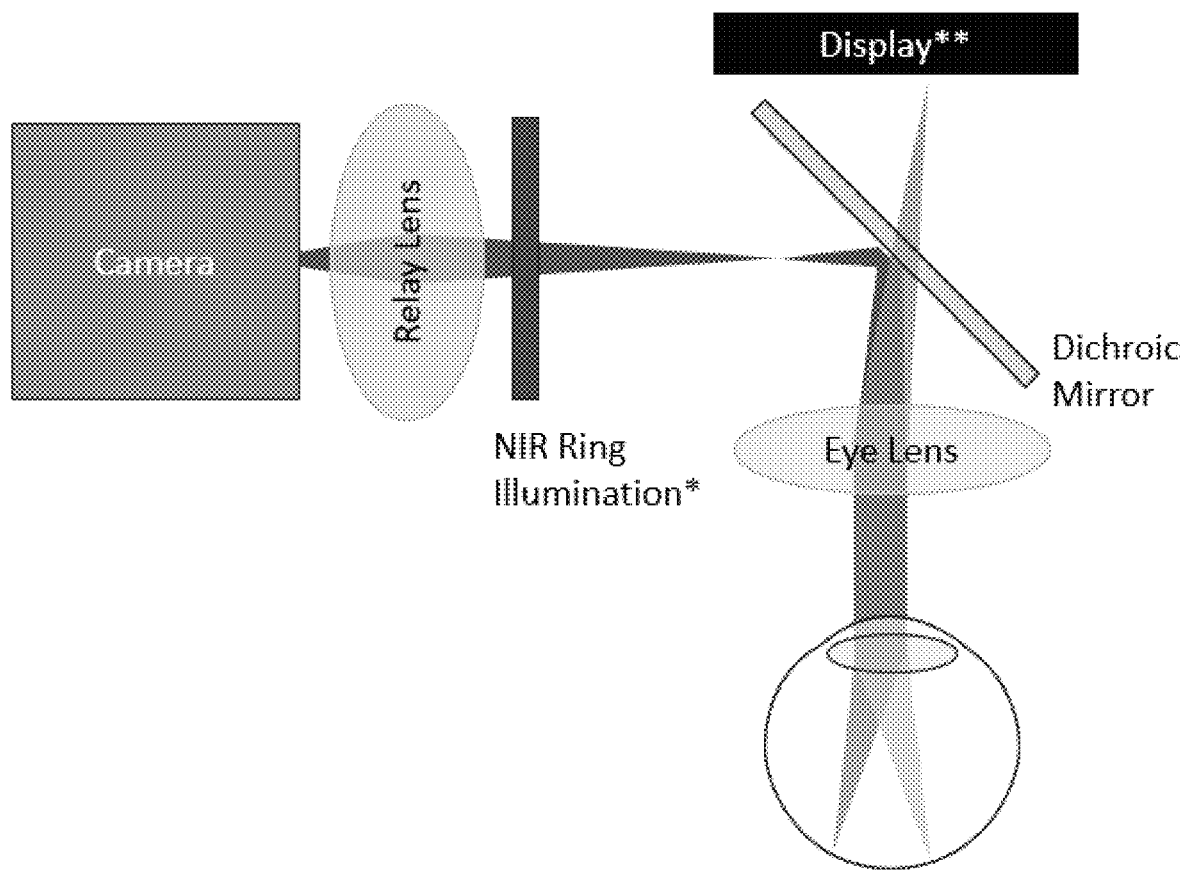
FIG. 3 shows a diagram of a retinal imaging system, according to an embodiment of the subject invention.

FIG. 3 shows a diagram of a retinal imaging system, according to an embodiment of the subject invention, in which fundoscopy is integrated with a HUD. The fundoscopy can be, for example, NIR fundoscopy, though embodiments are not limited thereto. Referring to FIG. 3, the system can include a HUD, a camera, a relay lens, and a ring illumination (e.g., an NIR ring illumination). The system can further include a dichroic mirror, which may be part of the HUD. If the ring illumination provides wavelength dependent illumination, the system can be configured (and able) to perform spectral imaging in the NIR wavelength region. The display (i.e., the HUD or a display that is part of the HUD) can provide stimulation (e.g., via regional illumination) to the retina, and the NIR fundoscopy can detect stimulation-induced hemodynamic changes. The system can further include a processor and/or machine-readable medium in operable communication with the HUD and/or the camera; the processor and the machine-readable medium can be in operable communication with each other. The machine-readable medium can have instructions stored thereon that, when executed by the processor, perform analysis of the data received from the camera and/or the HUD. The system can also include a display (different from the HUD) for displaying results of the analysis.

Figure 4:
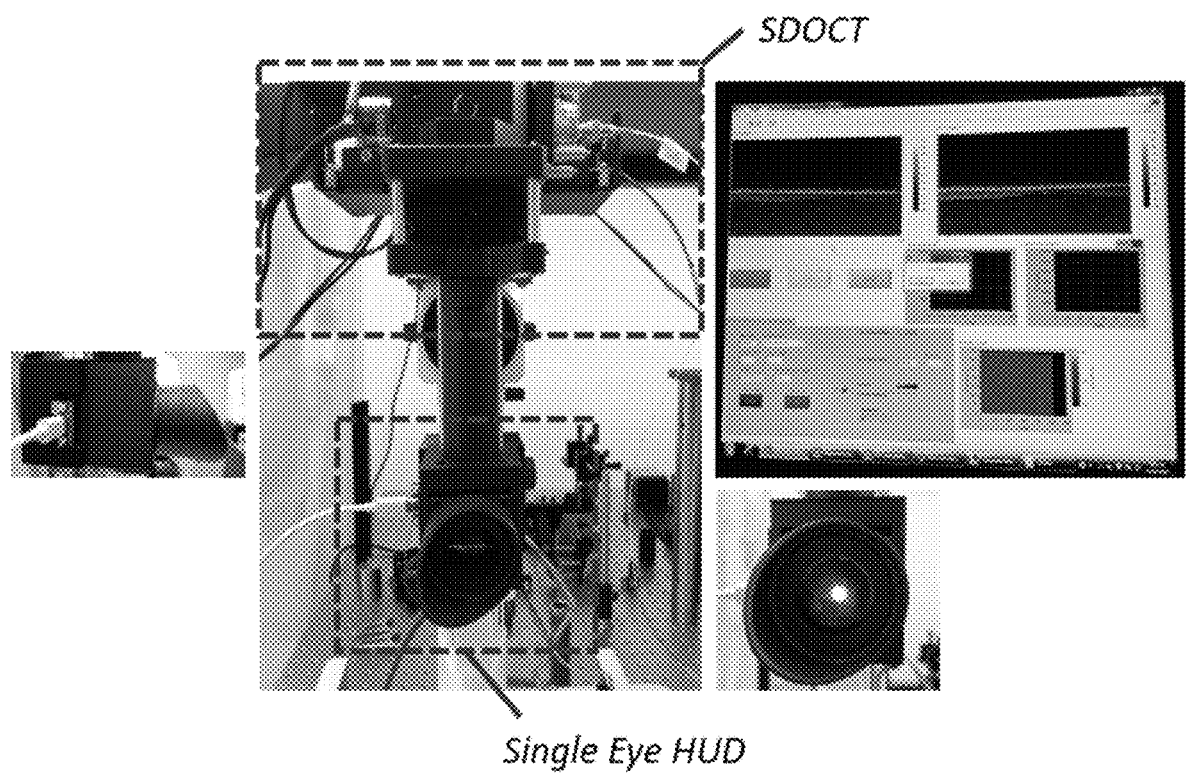
FIG. 4 shows an image of a retinal imaging system, according to an embodiment of the subject invention.

FIG. 4 shows an image of a retinal imaging system, according to an embodiment of the subject invention, comprising a spectral domain OCT (SDOCT) device integrated with a single-eye HUD. The system can include a processor and/or machine-readable medium in operable communication with the SDOCT device and/or the HUD, along with a display (different from the HUD) for displaying results of the analysis (seen in the upper-right of FIG. 4).

Modern retinal imaging modalities can analyze both the anatomical and functional characteristics of the retina. Also, modern retinal imaging modalities provide an opportunity to study neurovascular coupling, which may play a critical role in the early diagnosis of various neurological disorders.

Retinal imaging is crucial for several reasons, primarily due to its role in early detection, monitoring, and management of eye and systemic diseases. It allows for the early identification of conditions such as diabetic retinopathy, glaucoma, and age-related macular degeneration, often before symptoms appear, which is vital for effective treatment and preventing or inhibiting vision loss. Additionally, retinal imaging provides a baseline for tracking changes in the retina over time, enabling healthcare providers to monitor the progression of chronic eye diseases and adjust treatment plans accordingly. The retina can also reveal signs of systemic conditions like diabetes, hypertension, and certain cardiovascular diseases, making early detection through retinal imaging important for better overall health management.

Due to the unique optical properties of the eye, the retina is directly accessible to optical imaging techniques, which offer significantly higher resolution in the micrometer range and a wider array of contrast options compared to magnetic resonance imaging (MRI), functional MRI (fMRI), or computed tomography (CT). This accessibility allows for detailed visualization and analysis of retinal structures, making optical imaging an invaluable tool in diagnosing and managing various eye conditions. Moreover, the non-invasive nature of these optical imaging techniques greatly minimizes patient discomfort during examinations. Further, by visually demonstrating the condition of the retina, retinal imaging helps educate patients about their eye health, empowering them to take an active role in their treatment and care.

Retinal imaging technologies encompass a variety of advanced techniques that have significantly enhanced the diagnosis and management of retinal diseases. OCT is used for providing cross-sectional images of the retina, aiding in the diagnosis of conditions like diabetic macular edema and age-related macular degeneration by measuring retinal thickness and detecting fluid buildup. Optical coherence tomography angiography (OCTA) offers non-invasive, high-resolution images of retinal blood vessels, facilitating the assessment of blood flow and vascular health. Scanning laser ophthalmoscopy (SLO) uses a laser to create high-resolution images of the retina, often in combination with other techniques for comprehensive evaluations. Fundus photography captures images of the retina, optic nerve, and macula, essential for documenting and monitoring retinal conditions. Fluorescein angiography (FA), though invasive, is instrumental in visualizing blood flow and detecting vascular abnormalities. Fundus autofluorescence (FAF) detects natural retinal fluorescence to identify and monitor diseases without dye. Laser Doppler velocimetry (LDV) and Laser Doppler flowmetry (LDF) measure blood flow velocities in retinal arterioles and venules through the optical Doppler shift. These modalities have revolutionized retinal diagnostics by providing detailed insights into retinal structure and perfusion, enabling early detection and improved management of retinal diseases.

Retinal imaging technologies have greatly enhanced the diagnosis and management of a wide range of eye conditions, including macular edema, age-related macular degeneration, glaucoma, retinal detachment, diabetic retinopathy, optic nerve disorders, and abnormalities such as drusen and epiretinal membranes. Technologies capable of measuring blood flow, such as an OCTA, are particularly valuable for assessing neovascularization and detecting blood vessel blockages.

The rationale for using retinal imaging to assess neurological disorders lies in the unique anatomical and developmental characteristics of the retina, which is an extension of the central nervous system (CNS). Functional retinal imaging, particularly of neuronal activity, is of great interest because it allows for non-invasive observation of the CNS in living humans. The retina shares similarities with the CNS, including its neuronal circuitry, specialized immune response, and blood-retina barrier, making it an ideal proxy for studying the CNS and peripheral nerves. By imaging the retina, researchers can gain valuable insights into neuronal function and the wiring of the CNS.

Intrinsic optical signals (IOSs) offer promising potential for detecting neuronal activities in the retina, as demonstrated in ex vivo and animal studies across various retinal layers, including the photoreceptor outer segments and plexiform layers. IOS changes typically encompass various types of stimulus-induced optical property alterations, such as momentary light scattering, polarization, and absorption fluctuations in excitable tissues and cells. It has been suggested that IOSs should be detectable in other retinal layers as well. However, the primary limitation in applying this technique to humans is that the activation potentials of neurons produce only minor optical changes, which are challenging to detect. Additionally, inevitable eye movements cause optical path length changes, complicating the measurement of these small optical changes. While IOSs have been primarily observed in human photoreceptor cells, there has been limited research on the neuronal layers of the retina.

Neural activity in the retina, triggered by stimuli, can also be assessed by observing the resulting hemodynamic and metabolic changes. OCT can be used to record stimulus-evoked IOSs and hemodynamic alterations. Consistent and significant changes in IOSs at the photoreceptor outer segments can be reliably detected using OCT. Time-lapse OCT angiography, a functional extension of OCT, can be used to demonstrate hemodynamic changes in the retina triggered by light stimuli. Doppler OCT and fundus imaging can be used to measure changes in retinal blood flow, as well as variations in vessel diameter and velocity, in response to different light stimuli and oxygen levels.

OCT and OCTA are promising non-invasive technologies for diagnosing Alzheimer's disease (AD), but further research is needed to identify specific structural or microvascular changes in the retina and optic nerve that differentiate AD from other neurodegenerative diseases. The development of sensitive and specific OCT/OCTA parameters is essential for their clinical application in detecting AD. In addition to OCT and OCTA, other high-resolution ocular imaging techniques, such as widefield fundus photography, fluorescence lifetime imaging ophthalmoscopy, fundus autofluorescence, confocal scanning laser ophthalmoscopy, and retinal oximetry, have also been explored for studying AD-related ocular changes.

A significant limitation in evaluating these retinal imaging techniques is that their specificity to, for example, AD, cannot be established without conducting within-subject, longitudinal studies that include histology- and/or biomarker-confirmed diagnostic criteria. Also, the presence of multiple pathologies, such as cardiovascular and cerebrovascular issues, can complicate the assessment of retinal and cerebral pathology, serving as potential confounders.

Embodiments of the subject invention address the limitations discussed above and can be used to diagnose retinal and neurological diseases, including but not limited to diabetic retinopathy, glaucoma, retinitis pigmentosa, hypertensive retinopathy, retinopathy of prematurity, AD, multiple sclerosis, Parkinson's disease, and amyotrophic lateral sclerosis. Embodiments of the subject invention can also be used for visual function tests, including but not limited to amblyopia, squint, vision field inspection, and distortion.

Embodiments of the subject invention can also be used for vision science and psychophysical studies, such as exploring the correlation between physical stimulation and perception (mental processes). The relationship between vision science and psychology is both substantial and multidisciplinary. Vision science primarily focuses on understanding how visual systems operate, both in humans and in other organisms. It delves into the biological and physiological processes behind how we perceive, process, and interpret visual information. Psychology, particularly cognitive psychology, intersects with vision science in understanding how visual perception influences and is influenced by mental processes. Key areas of intersection include the following.

Perception and Cognition: Psychology examines how the brain interprets visual stimuli, leading to perception. This involves understanding how subjects recognize shapes, colors, depth, motion, and patterns, and how these perceptions integrate with cognitive processes like memory and decision-making.

Visual Attention: Both fields study how subjects focus on specific visual stimuli while ignoring others. This includes understanding why certain visual aspects capture a subject's attention and how this influences the subject's behavior and cognitive processing.

Visual Illusions: The study of visual illusions, where what a subject see differs from physical reality, is another area of overlap. These phenomena provide insights into the workings of the visual system and the psychological processes behind perception.

Eye Movements and Reading: The study of how subjects move their eyes to gather visual information, such as during reading, is another intersection. This includes understanding the cognitive processes behind eye movement control.

Developmental Aspects: Both fields also look at how visual perception develops from infancy into adulthood, providing insights into the maturation of visual and cognitive systems.

Neuroscience of Vision: The neural basis of vision is a crucial area where vision science and psychology converge. This involves understanding how the brain processes visual information and how this relates to behavior and cognitive processes.

Applications: In applied settings, knowledge from both fields is used in designing better visual displays, improving reading comprehension, developing therapies for visual disorders, and enhancing user experience in technology.

Thus, vision science provides the foundational understanding of the visual system while psychology applies this knowledge to understand how it influences and interacts with cognitive processes, behavior, and development. The integration of these fields contributes significantly to a comprehensive understanding of visual perception and cognition The domain of perception and cognition involves a detailed exploration of how visual information is processed and interpreted by the brain to form perceptual experiences. This includes the following.

Visual Processing Stages: Perception begins with the sensory processing of visual stimuli. Light enters the eye, is focused on the retina, and converted into neural signals. These signals are then transmitted to the brain, specifically to the primary visual cortex, where the process of interpreting visual information begins.

Feature Detection: The brain decodes basic visual features like color, shape, size, and motion. Specialized neurons in the visual cortex are responsible for detecting specific features. For instance, some neurons are tuned to respond to specific colors or orientations.

Pattern Recognition and Object Identification: Higher-level processing involves recognizing patterns and identifying objects. This includes integrating different features into coherent objects and using prior knowledge and context to interpret what is seen. For example, recognizing a chair involves not just seeing its shape and color but also understanding its function and context.

Depth and Spatial Perception: The brain interprets visual cues to understand the spatial layout of the environment. This includes depth perception, which allows judgement of distances and the three-dimensional structure of objects.

Visual Memory and Learning: Interaction between perception and cognitive processes includes the role of memory. Our ability to recognize and categorize visual stimuli is influenced by previous experiences and learned information.

Attention and Visual Processing: Cognitive psychology also explores how attention influences perception. Attention can enhance the processing of certain stimuli while filtering out irrelevant information, affecting what is consciously perceived.

Cognitive Biases and Expectations: Expectations and biases can shape perception. For instance, what is expected to be seen in a given context can influence how visual information is interpreted.

Multisensory Integration: Perception is not just about visual information. The brain integrates visual data with information from other senses (like auditory or tactile information) to form a more comprehensive understanding of the environment.

Neurological and Psychological Disorders: Studying abnormalities in perception, such as in visual agnosias or conditions like schizophrenia, provides insights into how normal visual cognition functions.

Cultural and Individual Differences: Perceptual experiences can vary between individuals and cultures, indicating the influence of environmental and social factors on how visual information is processed.

Hence, the interaction between perception and cognition in vision science and psychology is about understanding not just how subjects see, but how they interpret and make sense of what they see, influenced by a complex interplay of sensory input, neural processing, memory, attention, and context.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for retinal imaging, comprising:
   a retinal imaging device; and
   a heads-up display (HUD) disposed proximate to the retinal imaging device,
   the HUD being configured to provide a fixation target for a patient during retinal imaging,
   the HUD being configured to provide stimulation to the patient during retinal imaging,
   the stimulation comprising light at a plurality of wavelengths and a plurality of intensities,
   the retinal imaging device being a fundoscopy device,
   the fundoscopy device comprising a camera, and
   the system further comprising a relay lens and a near infrared (NIR) ring illumination element disposed between the camera and the HUD.

2. The system according to claim 1, further comprising a dichroic mirror configured to reflect light from an eye of the patient to the retinal imaging device during retinal imaging.

3. The system according to claim 1, the HUD being a two-eye HUD.

4. The system according to claim 1, the HUD being a one-eye HUD.

5. A method for retinal imaging on a patient, the method comprising:
   providing a retinal imaging device;
   disposing a heads-up display (HUD) to provide a fixation target for the patient and to provide stimulation to an eye of the patient, the stimulation comprising light at a plurality of wavelengths and a plurality of intensities; and
   operating the retinal imaging device to receive light reflected from the eye of the patient,
   the retinal imaging device being a fundoscopy device,
   the fundoscopy device comprising a camera, and
   the method further comprising disposing, between the camera and the HUD, a relay lens and a near infrared (NIR) ring illumination element.

6. The method according to claim 5, further comprising disposing a dichroic mirror between the eye of the patient and a display screen of the HUD,
   the dichroic mirror reflecting the light from the eye of the patient to the retinal imaging device.

7. The method according to claim 5, further comprising, before operating the retinal imaging device, using the HUD for dark adaptation of the patient.

8. A system for retinal imaging, comprising:
   a retinal imaging device;
   a heads-up display (HUD) disposed proximate to the retinal imaging device;
   a relay lens disposed between the retinal imaging device and the HUD; and
   a dichroic mirror configured to reflect light from an eye of a patient to the retinal imaging device during retinal imaging,
   the HUD being configured to provide a fixation target for a patient during retinal imaging,
   the HUD being configured to provide stimulation to the patient during retinal imaging,
   the stimulation comprising light at a plurality of wavelengths and a plurality of intensities,
   the retinal imaging device being a fluorescence fundoscopy device comprising a camera, and
   the system further comprising a near infrared (NIR) ring illumination element disposed between the camera and the HUD.

* * * * *